(12) United States Patent
Alizon et al.

(10) Patent No.: US 11,700,874 B2
(45) Date of Patent: Jul. 18, 2023

(54) INDUCTIVELY HEATABLE CONSUMABLE FOR AEROSOL GENERATION

(71) Applicant: JT International S.A., Geneva (CH)

(72) Inventors: Robert Alizon, Aubonne (CH); Peter Uhrmeister, Trier (DE); Andrew Rogan, Forres (GB)

(73) Assignee: JT International S.A.

( * ) Notice: Subject to any disclaimer, the term of this patent is extended or adjusted under 35 U.S.C. 154(b) by 259 days.

(21) Appl. No.: 16/957,644

(22) PCT Filed: Dec. 21, 2018

(86) PCT No.: PCT/EP2018/086525
§ 371 (c)(1),
(2) Date: Jun. 24, 2020

(87) PCT Pub. No.: WO2019/129693
PCT Pub. Date: Jul. 4, 2019

(65) Prior Publication Data
US 2020/0323271 A1    Oct. 15, 2020

(51) Int. Cl.
*A24F 13/00* (2006.01)
*A24B 3/14* (2006.01)
*A24F 40/48* (2020.01)
*A24F 40/465* (2020.01)
*H05B 6/10* (2006.01)
*A24C 5/01* (2020.01)
*A24D 1/20* (2020.01)
*A24F 40/20* (2020.01)

(52) U.S. Cl.
CPC .............. *A24B 3/14* (2013.01); *A24C 5/01* (2020.01); *A24D 1/20* (2020.01); *A24F 40/465* (2020.01); *A24F 40/48* (2020.01); *H05B 6/105* (2013.01); *A24F 40/20* (2020.01)

(58) Field of Classification Search
CPC ........................................................ A24F 47/00
USPC .................................................. 131/328–329
See application file for complete search history.

(56) References Cited

U.S. PATENT DOCUMENTS

| 5,613,505 A | 3/1997 | Campbell et al. |
| 11,241,032 B2 | 2/2022 | Garcia Garcia et al. |
| 2008/0199574 A1 | 8/2008 | Iodice et al. |

(Continued)

FOREIGN PATENT DOCUMENTS

| CN | 1564744 A | 1/2005 |
| CN | 202104213 U | 1/2012 |

(Continued)

OTHER PUBLICATIONS

Extended European Search Report including Written Opinion for Application No. EP17211198.1, dated Jul. 6, 2018, pp. 1-9.

(Continued)

*Primary Examiner* — Phuong K Dinh
(74) *Attorney, Agent, or Firm* — Lerner David LLP

(57) ABSTRACT

An inductively heatable consumable for aerosol generation includes an aerosol forming substrate in the form of particles and a susceptor in the form of a plurality of particles, wherein the susceptor is a combination of an aerosol forming substrate and a susceptor for obtaining a rigid susceptor, wherein the rigid aerosol forming substrate layer has a rigidity greater than the rigidity of the susceptor layer.

27 Claims, 2 Drawing Sheets

(56) References Cited

U.S. PATENT DOCUMENTS

| | | |
|---|---|---|
| 2011/0088707 A1 | 4/2011 | Hajaligol |
| 2016/0150825 A1 | 6/2016 | Mironov et al. |
| 2016/0295921 A1 | 10/2016 | Mironov et al. |
| 2017/0055582 A1 | 3/2017 | Blandino et al. |
| 2017/0064996 A1 | 3/2017 | Mironov |
| 2017/0079325 A1 | 3/2017 | Mironov |
| 2017/0119049 A1 | 5/2017 | Blandino et al. |
| 2017/0119050 A1 | 5/2017 | Blandino et al. |
| 2017/0150755 A1 | 6/2017 | Batista |
| 2018/0070625 A1 | 3/2018 | Voss et al. |
| 2018/0184713 A1 | 7/2018 | Mironov et al. |
| 2018/0271153 A1 | 9/2018 | John et al. |
| 2018/0317286 A1* | 11/2018 | Rojo-Calderon ..... A24F 40/485 |
| 2019/0008210 A1 | 1/2019 | Mironov et al. |

FOREIGN PATENT DOCUMENTS

| | | |
|---|---|---|
| CN | 105307516 A | 2/2016 |
| CN | 105407750 A | 3/2016 |
| CN | 106455704 A | 2/2017 |
| CN | 106488714 A | 3/2017 |
| CN | 105428206 B | 7/2017 |
| CN | 107427086 A | 12/2017 |
| EP | 1423279 A2 | 6/2004 |
| JP | H08511175 A | 11/1996 |
| JP | H8511176 A | 11/1996 |
| JP | 2015517819 A | 6/2015 |
| JP | 2016526873 A | 9/2016 |
| JP | 2016532432 A | 10/2016 |
| TW | 201601600 A | 1/2016 |
| WO | 9527412 A1 | 10/1995 |
| WO | 2013178768 A1 | 12/2013 |
| WO | 2015177252 A1 | 11/2015 |
| WO | 2015177255 A1 | 11/2015 |
| WO | 2015177264 A1 | 11/2015 |
| WO | 2015177265 A1 | 11/2015 |
| WO | 2016107766 A1 | 7/2016 |
| WO | 2016184674 A1 | 11/2016 |
| WO | 2017005705 A1 | 1/2017 |
| WO | 2017068091 A1 | 4/2017 |
| WO | 2017068093 A1 | 4/2017 |
| WO | 2017178394 A1 | 10/2017 |

OTHER PUBLICATIONS

International Search Report from Application No. PCT/EP2018/086528 dated Apr. 12, 2019, 4 pages.

International Search Report including Written Opinion for Application No. PCT/EP2018/086525, dated Apr. 2, 2019, pp. 1-18.

Search Report dated Dec. 27, 2022 from the Office Action for Chinese Application No. 201880081640.6 issued Jan. 5, 2023, 3 pages. [See p. 2, categorizing the cited references].

Search Report dated Oct. 19, 2022 from the Office Action for Chinese Application No. 201880084852.X issued Oct. 26, 2022, pp. 1-3.

Search Report completed Jul. 17, 2022 from Office Action for TW Application No. 107146340 dated Jul. 20, 2022. 1 pg.

* cited by examiner

INDUCTIVELY HEATABLE CONSUMABLE FOR AEROSOL GENERATION

CROSS-REFERENCE TO RELATED APPLICATIONS

The present application is a national phase entry under 35 U.S.C. § 371 of International Application No. PCT/EP2018/086525, filed Dec. 21, 2018, published in English, which claims priority to European Application No. 17211198.1 filed Dec. 29, 2017, the disclosures of which are incorporated herein by reference.

TECHNICAL FIELD

The present disclosure relates to an inductively heatable consumable for aerosol generation. The consumable is especially suitable for use in an inductive heating device for aerosol generation. Embodiments of the present disclosure also relate to a method of manufacturing an inductively heatable consumable and an aerosol generating device.

TECHNICAL BACKGROUND

Devices which heat, rather than burn, a vaporisable substance to produce a vapour for inhalation have become popular with consumers in recent years.

In electrically heatable smoking devices for example a tobacco plug made of a tobacco sheet containing tobacco particles and glycerine as aerosol former is heated by a heatable blade. In use, the tobacco plug is pushed onto the blade such that the plug material is in close thermal contact with the heated blade. In aerosol generating devices, the tobacco plug is heated to evaporate the volatile compounds in the plug material, preferably without burning the tobacco as in conventional cigarettes. However, in order to heat remote peripheral regions of a plug for aerosol generation, the material proximate to the heating blade has to be excessively heated such that burning of tobacco in the vicinity of the blade may not entirely be prevented.

It has been proposed to use inductive heating for an aerosol forming substrate. It has also been proposed (as in WO2015/177252) to provide an inductively heatable tobacco product in the form of a crimped tobacco sheet within which discrete small particles of susceptor are dispersed.

However, this solution has several shortcomings for example a shortcoming may be the difficulty to manipulate small particles of susceptor. Another shortcoming may be the difficulty to homogeneously distribute or blend these small particles within the crimped tobacco material sheet, knowing that usually for cost reasons these particles of susceptor are very thin. Thus increasing also the difficulty of manipulation of these particles during the manufacturing process of the tobacco product (as in WO2017/178394). In addition, rendering difficult to obtain a homogeneous heat from the susceptor to the tobacco material. Thus, an optimized aerosol generation from the tobacco product. Therefore, there is need to address these shortcomings.

SUMMARY OF THE DISCLOSURE

According to a first aspect of the present disclosure, there is provided an inductively heatable consumable for aerosol generation. The consumable comprising flavour forming particles and a susceptor in the form of a plurality of susceptor particles. Each susceptor particle is a combination of a rigid aerosol forming substrate layer and a susceptor layer for obtaining a rigid susceptor particle, wherein the rigid aerosol forming substrate layer has a rigidity greater than the rigidity of the susceptor layer Preferably the rigidity of each rigid susceptor particle is substantially the same as the rigidity of the substrate layer.

It will be appreciated by the person skilled in the art that in this case there is provided an inductively heatable consumable (100) for aerosol generation, the consumable (100) comprising flavour forming particles and a susceptor in the form of a plurality of susceptor particles, wherein each susceptor particle is a combination of a rigid aerosol forming substrate layer (102) and a susceptor layer (104) for obtaining a rigid susceptor particle (106) having a rigidity substantially equivalent to the rigidity of the substrate with which it is combined. Such an inductively heatable consumable is therefore also an aspect of the present invention separately hereby disclosed. This may be achieved, for example, by providing the substrate layer with a rigidity and/or strength which is sufficiently great compared to the rigidity and/or strength of the susceptor layer that the contribution from the susceptor layer to the overall rigidity of the rigid susceptor particle (which is a combination of the substrate layer and the susceptor layer) is small or negligible.

Preferably the rigidity of the combination i.e. of the obtained rigid susceptor particle is no more than 110% of the rigidity of the substrate layer (i.e. the combination should not be more than 10% more rigid than the substrate layer alone) and more preferably the combination should be no more than 105% of the rigidity of the substrate layer alone. Most advantageously, the rigid susceptor particle may have a rigidity equivalent to the rigidity of the substrate with which the susceptor layer is combined within no more than a 1% difference. This may conveniently be achieved if using a very thin susceptor layer e.g. less than 50 microns (note common aluminium foil used in cooking typically has relatively low rigidity and varies in thickness between about 6 microns up to about 200 microns).

The tobacco aerosol forming substrate gives to the susceptor the rigidity that it needs to allow easy manipulation of the susceptor particles. The tobacco aerosol forming substrate gives to the susceptor the rigidity that it needs to facilitate the blending of the particles of rigid susceptor with the particles of aerosol forming substrate. Thus, leading to a homogeneous distribution of the rigid particles of susceptor through the particles of the aerosol substrate. Thus, optimizing aerosol generation.

The shear strength of the susceptor particles may be at least 250 mega-Pascal (MPa) and/or the cut-width of the susceptor may be as desired (for example at least 0.5 millimetres) such as to minimise the risk of the particles curling under the normal stresses incurred during typical cigarette manufacturing processes. This minimises curling of the susceptor layer or the combined substrate and susceptor layers forming each susceptor particle. In turn this reduces hot-spots being formed during heating of the consumable because the reduced curling limits deformation of susceptor particles keeping the distance between the susceptor particles more uniform than if more curling were to occur. For example, we have found curling is reduced by increasing the cut-width.

Furthermore, the aerosol forming substrate layer may be made to withstand the (high) temperatures produced by the susceptor elements when being inductively heated (whilst generating vapour from vaping agents such as Glycerine, Propylenglycol, Tobacco Flavours and their combinations when activated by the susceptors) and may insulate the normal tobacco from direct contact with the hot susceptors which could otherwise burn the normal tobacco.

The rigid sheet may comprise a first at least aerosol forming substrate sheet, a susceptor sheet. In this case, the sheets of susceptor and aerosol forming substrate are arranged for adhering together. The aerosol forming substrate sheet thus enhances the rigidity of the thin susceptor layer. The susceptor layer is well bound on the substrate and it is not subjected to slip.

Each susceptor layer and each substrate layer of each susceptor particle may be at least part (i.e. all or part) of respective pre-formed (solid) sheets. The susceptor layer and substrate layer of each susceptor particle may have aligned outer (i.e. external) perimeters. Said outer perimeters may be parallel to each other and may be provided by an external face of each of said layers that have an aligned normal (i.e. a geometric normal) to the respective faces.

It is preferable if the substrate layer has the desired rigidity before it is combined with the susceptor layer. The plurality of susceptor particles may be a uniform size and/or shape and/or volume. This allows more uniform heating to be provided when using a plurality of particles, thereby avoiding hot-spots in heating, and as such reducing the risk of burning any material during heating.

Each susceptor particle may be a sheared susceptor particle. By this we intend to mean the particular has undergone shear deformation, for example due to cutting. Each susceptor layer and/or each substrate layer may respectively be a sheared susceptor layer and/or a sheared substrate layer. To produce such particles or layers, the layers need to be shearable, meaning they must have a defined shape, such as by virtue of being a solid instead of a non-solid, for example: a liquid or liquid like material like a slurry. By being shearable, more rapid production of the particles/layer(s) is possible since no solidifying step is needed in the production of the particles/layer(s). This also means the aerosol and/or moisture content of the susceptor is not reduced during by the production process, allowing the susceptor/layer(s) to retain their original properties and not become degraded by the production process. Further, by being sheared, the shape of the particles/layers is more uniform. As set out above, improved uniformity allows more uniform heating to be provided when using a plurality of particles. This provides the benefits set out above.

The inductively heatable consumable may include perforations which extend through the sheets of aerosol forming substrate and of susceptor. The perforations advantageously facilitate air flow through the inductively heatable consumable during use in an aerosol generating device and may advantageously improve heating efficiency due to the skin effect. The perforations allow the porosity, and hence the air permeability, of the resultant inductively heatable consumable to be carefully controlled and optimised. For example, the consumable may have an air permeability of about 50 to about 20,000 CORESTA Units (CU) ±10% (one CORESTA Unit being the volumetric flow rate of air, in centimetres cubed per minute, $cm^3$/min, passing through a 1 centimetre sample of substrate at an applied pressure difference of 1 kilo Pascal, kPa).

Alternatively, the rigid susceptor may further comprise a second aerosol forming substrate sheet. In this case, the rigid susceptor and the second aerosol forming substrate sheet are arranged for adhering together for obtaining a second rigid susceptor sheet. In this arrangement, the second rigid sheet preferably has a rigidity substantially equivalent to or more than the rigidity of the susceptor sheet. This has the advantage to further increase the rigidity of the combination (i.e. of the first and second substrate sheets in combination with the susceptor sheet. This in turn provides for increased rigidity of the resulting susceptor particles, thus, facilitating the blending of the susceptor particles with the particles of aerosol forming substrate. Thus, increasing the homogeneity of the mixture. Thus, optimizing the aerosol generation.

The susceptor may be embedded in the aerosol forming substrate for forming the rigid susceptor sheet. This allows the susceptor to bind well to the aerosol forming material and it is not subject to slip.

An adhesive may be provided between each susceptor layer and each respective substrate layer. This provides a means of attaching the layers of each susceptor particle together. The adhesive may be provided by a material other than the material of the susceptor layer and substrate layer.

According to the invention, the term adhering or combining or embedded may include technologies amongst: printing, gluing, stacking, binding, sticking.

According to the invention the particles of susceptor may be obtained by cutting the first or the second rigid susceptor sheet in form of particles.

According to the invention, the particles of the first rigid susceptor sheet and the particles of aerosol forming substrate may be mixed together for obtaining a substantially homogeneous mixture (i.e. with susceptor particles approximately evenly distributed within the mixture). The substantially homogeneous distribution of the particles of rigid susceptor and the aerosol substrate allows an optimized aerosol generation.

Alternatively, the particles of the second rigid susceptor sheet and the particles of aerosol forming substrate may be mixed together to obtain a substantially homogeneous mixture. The homogeneous/even distribution of the particles of rigid susceptor and the aerosol substrate allows an optimized aerosol generation.

The susceptor within the consumable typically has the ability to convert energy transferred as an alternating magnetic field into heat. The amount of heat which the susceptor (i.e. the sum of the susceptor particles) is able to generate in this way is referred to as the heating capability. The heating capability is the capability of the susceptor, and in particular the susceptor layer, to transfer heat to the surrounding aerosol forming substrate/material.

The susceptor layer typically predominantly conductively heats the intimately contacting or proximal aerosol forming material and aerosol former within the adjacent rigid aerosol forming substrate sheet(s). The intimate thermal contact between the susceptor layer and the aerosol forming substrate sheet(s) prevents the susceptor layer from reaching temperatures much in excess of the temperature of the adjacent rigid aerosol forming substrate sheet(s), which temperature is substantially maintained near the boiling point of the aerosol forming substrate (i.e. the boiling point of the humectant such as vegetable glycerol and/or propylene glycol contained within the aerosol forming substrate sheet). The susceptor particles may not be in intimate thermal contact with other elements of the mixture (e.g. surrounding aerosol forming particles such as tobacco particles) and so heat conductance to those particles may be fairly small, but the vapour generated from the aerosol forming substrate layer in intimate thermal contact with the susceptor layer will efficiently heat the surrounding particles by convection thus quickly bringing the surrounding particles to the temperature at which they produce volatile components, that can become entrained in the vapour generated from the aerosol forming substrate, to evolve the desired flavours and other desired components such as nicotine. Thus, the heating capability depends upon the material and the extent of the thermal contact between the susceptor layer and its adjacent aerosol forming substrate sheet. Preferably, the surrounding particles may be specially treated tobacco particles such as those found in hybrid devices known in the art such as the Ploom Tech® device in order to make the desired flavour and stimulant components readily entrained within a passing vapour and/or condensation aerosol formed from the vapour.

In the consumable according to the invention, the particles of rigid susceptor are preferably homogeneously distributed in the particles of aerosol forming substrate. By this, a uniform heating capability in the aerosol forming substrate may be achieved, thus generating a uniform heat distribution in the aerosol forming substrate and in the consumable leading to a uniform temperature distribution in the consumable.

Uniform or homogeneous temperature distribution of the consumable is herein understood as a consumable having a substantially similar temperature distribution over a cross section of the consumable. This optimizes the aerosol vapour generation. Preferably, the consumable may be heated such that temperatures in different regions of the consumable, such as for example central regions and peripheral regions of the consumable, differ by less than 50 percent, preferably by less than 30 percent.

According to the present invention, the shape of the particles of rigid susceptor and the shape of the particles of the aerosol forming substrate may include line, strand, polygonal such as little square, curve such as disc, oval, annulus, circle. Circular or annular shaped particles of rigid susceptor are especially preferred as they tend to generate eddy currents in response to an alternating magnetic field most effectively and thus result in increased heating capability of the consumable.

According to the present invention, the first or second aerosol forming substrate sheets may include tobacco, tobacco derivatives, expanded tobacco, tobacco extract, homogenized tobacco, tobacco substitutes or any combinations thereof. Preferably reconstituted tobacco paper that has the advantage to be easier to manufacture. The reconstituted tobacco type includes tobacco and any one or more of cellulose fibres, tobacco stalk fibres and inorganic fillers such as calcium carbonate (CaCO3).

According to the invention, the inductively heatable consumable for aerosol generation, the consumable may comprise a third aerosol forming substrate. The third aerosol forming substrate may be in the form of particles and a susceptor in the form of a plurality of particles, wherein the susceptor is a combination of an aerosol forming substrate and a susceptor for obtaining a rigid susceptor having a rigidity substantially equivalent to the rigidity of the substrate with which it is combined The third aerosol forming substrate sheet may include tobacco, tobacco derivatives, expanded tobacco, tobacco extract, homogenized tobacco, tobacco substitutes, reconstituted tobacco or any combinations thereof.

According to the invention the aerosol forming substrates may include one or more aerosol former. The aerosol-former may be any suitable known compound or mixture of compounds that, in use, facilitates formation of a dense and stable aerosol and that is substantially resistant to thermal degradation at the operating temperature of the inductive heating device.

Aerosol formers may be selected from the polyols, glycol ethers, polyol ester, esters, and fatty acids and may comprise one or more of the following compounds: glycerine, erythritol, 1,3-butylene glycol, tetraethylene glycol, triethylene glycol, triethyl citrate, propylene carbonate, ethyl laurate, triacetin, meso-Erythritol, a diacetin mixture, a diethyl suberate, triethyl citrate, benzyl benzoate, benzyl phenyl acetate, ethyl vanillate, tributyrin, lauryl acetate, lauric acid, myristic acid, 1,3-propanediol and propylene glycol.

According to the invention, the aerosol-forming substrate may comprise other additives and ingredients, such as flavourants. The aerosol-forming substrate preferably comprises nicotine and at least one aerosol-former. In a preferred embodiment, the aerosol-former is glycerine. The susceptor materials being in thermal proximity of the aerosol-forming substrate allow for a more efficient heating and thus, higher operating temperatures may be reached. The higher operating temperature enables glycerine to be used as an aerosol-former which provides an improved aerosol as compared to the aerosol-formers used in the known systems. In an embodiment of the aerosol-forming substrate according to the invention the second Curie-temperature of the second susceptor material may be selected such that upon being inductively heated an overall average temperature of the aerosol-forming substrate does not exceed 240° C. The overall average temperature of the aerosol-forming substrate here is defined as the arithmetic mean of a number of temperature measurements in central regions and in peripheral regions of the aerosol-forming substrate. By pre-defining a maximum for the overall average temperature the aerosol-forming substrate may be tailored to an optimum production of aerosol.

Average temperatures of the tobacco consumable may be about 30 degree Celsius to about 240 degrees Celsius. This has been found to be a temperature range where desired amounts of volatile compounds are produced, especially in tobacco sheet made of homogenized tobacco material or reconstituted tobacco with glycerine as aerosol former, especially in cast leaf as will be described in more detail below. At these temperatures no substantial overheating of individual regions of the consumable is achieved, although the susceptor particles may reach temperatures of up to about 400 to 450 degree Celsius.

Aerosol formers included in the aerosol forming substrate may be chosen based on one or more characteristics. Functionally, the aerosol former may provide a mechanism that allows it to be volatilized and convey nicotine or flavouring or both in an aerosol when heated above the specific volatilization temperature of the aerosol former. Different aerosol formers typically vaporize at different temperatures. An aerosol former may be chosen based on its ability, for example, to remain stable at or around room temperature but able to volatize at a higher temperature, for example, between 40 degree Celsius and 450 degree Celsius. The aerosol former may also have humectant type properties that help maintain a desirable level of moisture in an aerosol-forming substrate when the substrate is composed of a tobacco-based product including tobacco particles. In particular, some aerosol formers are hygroscopic material that functions as a humectant, that is, a material that helps keep a substrate containing the humectant moist.

One or more aerosol former may be combined to take advantage of one or more properties of the combined aerosol formers. For example, triacetin may be combined with glycerine and water to take advantage of the triacetin's ability to convey active components and the humectant properties of the glycerine.

According to the present invention, the particles of rigid susceptor sheet and the particles of aerosol forming substrates may range in length from 1 to 15 millimetres, preferably from 2 to 8 millimetres. Preferably each particle may have a similar size and shape and as far as possible in a consistent orientation relative to an induction coil.

Going back again to the susceptor, typically it is a conductor that is capable of being inductively heated. The susceptor is typically capable of absorbing electromagnetic energy and converting it to heat. In the tobacco consumable according to the invention, changing electromagnetic fields generated by one or several induction coils of an inductive heating device may heat the susceptor layers, which then transfer the heat to the aerosol-forming substrate of the tobacco product, mainly by conduction of heat. For this, the susceptor layer is in intimate thermal contact with the aerosol forming substrate layers and aerosol former contained therein. Due to the particulate nature of the susceptor, heat is produced according to the distribution of the particles in the tobacco particles.

In some preferred embodiments of the tobacco consumable according to the invention, the tobacco material may be reconstituted tobacco material and the aerosol former comprises glycerine. Preferably, the tobacco consumable is made of a reconstituted tobacco.

It has further been found that in order to provide sufficient heat for optimal aerosol formation but without burning the tobacco or the fibers, certain characteristics, including shape, rigidity and distribution throughout the other particles, of the susceptor particles may need to be carefully chosen for the susceptor particles to be suitable in combination with tobacco particles containing an aerosol former, and preferably containing glycerine as aerosol-former.

With an optimal selection and distribution of the particles in the tobacco particles, energy required for heating may be reduced. However, enough energy to release the volatile compounds from the substrate is still provided. Energy reduction may not only reduce energy consumption of an inductive heating device for aerosol generation the tobacco product is used with, but may also reduce the risk of overheating the aerosol-generating substrate. Energy efficiency is also achieved by achieving a depletion of aerosol former in the tobacco consumable in a very homogeneous and complete manner. Especially, also peripheral regions of a tobacco consumable may contribute to aerosol formation. By this, a tobacco consumable such as a tobacco consumable plug may be used more efficiently. For example, a smoking experience may be enhanced or the size of the tobacco consumable may be reduced by evaporating a same amount of volatile compounds from the tobacco product as in a conventionally more extensively heated or larger aerosol-forming substrate. Thus, cost may be saved and waste may be reduced.

According to certain embodiments of the tobacco consumable according to the invention, the particles of tobacco may have sizes in a range of about 5 micrometres to about 100 micrometres, preferably in a range of about 10 micrometres to about 80 micrometres, for example have sizes between 20 micrometres and 50 micrometres. Sizes in these ranges for particles have been found to be in an optimal range to allow for a homogenous distribution of the susceptor particles with the tobacco particles. Too small particles are not desired as they may pass through a filter, for example a conventional filter as used in smoking articles. Such filters may also be used in combination with the tobacco consumable according to the invention.

According to certain other embodiments of the invention, the particles of tobacco may have size of tobacco used in roll-your-own cigarettes (also called RYO, MYO, rollies, roll-ups, burns, hand-rolled cigarettes, or simply rolls).

According to an aspect of the invention, the tobacco particles can be sized as those found in hybrid devices known in the art such as the Ploom Tech® device in order to make the desired flavour and stimulant components readily entrained within a passing vapour and/or condensation aerosol formed from the vapour.

According to an aspect of the invention, the susceptor particles may be a bit bigger than the tobacco particles which can be like Ploom Tech® tobacco particles although could also be much bigger (like normal roll your own tobacco particles) while the little susceptor particles are preferably of the order of a few millimetres to enable them to generate a substantial eddy current when induced by an alternating electromagnetic field.

As mentioned above, the susceptor particles may preferably be shaped as flat discs (or annular discs) with diameters of between 1 to 15 millimetres or more preferably 2 to 8 millimetres and thicknesses of less than 1 millimetres. Larger particles render difficult or impossible a homogenous distribution in particles of tobacco. Larger particles may not be distributed in the tobacco particles as finely as smaller particles. In addition, larger particles tend to stick out of the tobacco particles, such that they may contact each other. This is unfavourable due to locally enhanced heat generation. The size of particles is herein understood as the equivalent spherical diameter. Preferably, the particles of susceptor have a similar size and shape and are, as far as possible, distributed within the tobacco particles in a consistent orientation relative to the induction coil (preferably with their planes orthogonal to a central axis of the driving inductor coil of the heating device for use with the consumable).

According to another aspect of the tobacco consumable according to the invention, the plurality of particles may amount to a range between about 4 weight percent and about 45 weight percent, preferably to between about 10 weight percent and about 40 weight percent, for example to 30 weight percent of the tobacco product. It will now be obvious to one of ordinary skill in the art that while various weight percent of susceptor are provided above, changes to the composition of the elements comprising the tobacco consumable, including the weight percent of tobacco, aerosol former, binders, and water will require adjustment of the weight percent of susceptor required to effectively heat the tobacco product.

Amounts of susceptor particles in these weight ranges relative to the weight of the tobacco consumable have been found to be in an optimal range to provide a homogeneous heat distribution over the entire tobacco consumable. In addition, these weight ranges of susceptor particles are in an optimal range to provide sufficient heat to heat the tobacco particles to a homogeneous and average temperature, for example to temperatures of between 200 degree Celsius and 240 degree Celsius.

According to another aspect of the tobacco consumable according to the invention, the susceptor particles may comprise or may be made of a sintered material. Sintered material provides a wide variety of electric, magnetic and thermal properties. Sintered material may be of ceramic, metallic or plastic nature. Preferably, for susceptor particles metallic alloys are used. Depending on the manufacturing process such sintered materials may be tailored to a specific application. Preferably, sinter material for the particles used in the tobacco product according the invention has a high thermal conductivity and a high magnetic permeability.

According to a further aspect of the tobacco consumable according to the invention, the particles may comprise an outer surface which is chemically inert. A chemically inert surface prevents the particles to take place in a chemical reaction or possibly serve as catalyst to initialize an undesired chemical reaction when the tobacco consumable is heated. An inert chemical outer surface may be a chemically inert surface of the susceptor material itself. An inert chemical outer surface may also be a chemically inert cover layer that encapsulates susceptor material within the chemically inert cover. A cover material may withstand temperatures as high as the particles are heated. An encapsulation step may be integrated into a sinter process when the particles are manufactured. Chemically inert is herein understood with respect to chemical substances generated by heating the tobacco consumable and being present in the tobacco consumable.

In some preferred embodiments of the tobacco consumable according to the invention, the particles may be made of ferrite. Ferrite is a ferromagnet with a high magnetic permeability and especially suitable as susceptor material. Main component of ferrite is iron. Other metallic components, for example, zinc, nickel, manganese, or non-metallic components, for example silicon, may be present in varying amounts. Ferrite is a relatively inexpensive, commercially available material. Ferrite is available in particle form in the size ranges of the particles used in the tobacco product according to the invention. Preferably, the particles are a fully sintered ferrite powder, such as for example FP350 available by Powder Processing Technology LLC, USA.

According to yet a further aspect of the tobacco product according to the invention, the susceptor may have a Curie temperature between about 200 degree Celsius and about 450 degree Celsius, preferably between about 240 degree Celsius and about 400 degree Celsius, for example about 280 degree Celsius.

Particles comprising susceptor material with Curie temperatures in the indicated range allow a rather homogeneous temperature distribution of the tobacco product to be achieved and an average temperature of between about 200 degree Celsius and 240 degree Celsius. In addition, local temperatures of the aerosol-forming substrate do generally not or not significantly exceed the Curie temperature of the susceptor. Thus, local temperatures may be below about 400 degree Celsius, below which no significant burning of the aerosol-forming substrate occurs.

When a susceptor material reaches its Curie temperature, the magnetic properties change. At the Curie temperature the susceptor material changes from a ferromagnetic phase to a paramagnetic phase. At this point, heating based on energy loss due to orientation of ferromagnetic domains stops. Further heating is then mainly based on eddy current formation such that a heating process is automatically reduced upon reaching the Curie temperature of the susceptor material. Reducing the risk of overheating the aerosol-forming substrate may be supported by the use of susceptor materials having a Curie temperature, which allows a heating process due to hysteresis loss only up to a certain maximum temperature. Preferably, susceptor material and its Curie temperature are adapted to the composition of the aerosol-forming substrate in order to achieve an optimal temperature and temperature distribution in the tobacco product for an optimum aerosol generation.

According to another variant of the invention, the consumable further may comprise a paper sheet wrapped around the homogeneous mixture for obtaining tobacco rod. The rod may have rod diameter in the range between about 3 millimetres to about 30 millimetres, preferably between about 8 millimetres to about 20 millimetres, for example 10 millimetres. The rod may have a rod length in the range between about 10 millimetres to about 100 millimetres, preferably between about 20 millimetres to about 50 millimetres, for example 30 millimetres. Preferably, the rod has a circular or oval cross-section. However, the rod may also have the cross-section of a rectangle or of a polygon.

To ease handling the consumable by a consumer, the rod may be provided in a tobacco stick that includes the rod, a filter, and a mouthpiece formed sequentially. The filter may be a material capable of cooling the aerosol formed from the rod material and may also be able to alter the constituents present in the aerosol formed. For example, if the filter is formed of a polylactic acid or of a similar polymer, the filter may remove or reduce phenol levels in the aerosol. The filter may also be capable of preferentially adhering to itself any large condensation droplets to prevent such droplets forming and adhering to the mouthpiece section; to achieve this it may for example include a rough or fabric-like surface as is known to persons skilled in the art. The rod, filter, and mouthpiece may be circumscribed with a paper having sufficient stiffness to facilitate the handling of the rod. The length of the tobacco stick may be between 20 millimetres and 110 millimetres, and preferably may be approximately 45 millimetres in length.

Accordingly, in another aspect of the invention, there may be provided a tobacco material containing unit, for example a tobacco stick, the unit comprising a tobacco consumable as described in this application and a filter. In this case, the tobacco consumable and the filter are aligned in an endwise manner and are wrapped with a sheet material, for example paper, for fixing filter and tobacco consumable in the tobacco material containing unit.

According to another variant of the invention, the consumable may further comprise a capsule arranged to receive the homogeneous mixture. The capsule may be arranged to be porous in at least one side to allow air flow.

According to another aspect of the present disclosure, there is provided an aerosol generating device comprising:
　　a heating compartment arranged to receive the consumable according to any previous aspect;
　　an induction heating assembly arranged to inductively heat said consumable.

According to another aspect of the present disclosure, there is provided a method of manufacturing an inductively heatable consumable for aerosol generation, the method comprising steps of:
　　providing an aerosol forming substrate sheet;
　　providing a susceptor sheet;
　　combining the susceptor sheet with the aerosol forming substrate sheet for obtaining a rigid sheet;
　　cutting the rigid sheet in small size of particles;
　　mixing said small particle with particles of aerosol forming substrate.

The rigid susceptor particle may have a rigidity greater than the rigidity of the susceptor sheet. Preferably, the rigid susceptor particle has a rigidity of no more than 110% of the rigidity of the substrate layer (i.e. the combination should not be more than 10% more rigid than the substrate layer alone) and most preferably the combination should be no more than 105% of the rigidity of the substrate layer alone. Most advantageously, the rigid susceptor particle may have a rigidity substantially equivalent to the rigidity of the substrate with which the susceptor layer is combined (e.g. being no more than say 1% more rigid than the rigidity of the substrate layer alone).

According to another aspect of the present disclosure, there is provided a method of manufacturing an inductively heatable consumable for aerosol generation, the method comprising steps of:

provviding a solid aerosol forming substrate sheet;
providing a susceptor sheet;
combining the susceptor sheet with the solid aerosol forming substrate sheet for obtaining a combined sheet;
cutting the combined sheet into susceptor particles;
mixing said susceptor particles with particles of aerosol forming substrate.

This has the advantage to increase the rigidity of the susceptor particles.

A method of manufacturing an inductively heatable consumable for aerosol generation, wherein before the step of cutting the rigid sheet in small size of particles, the method further comprising the step of:

providing a second aerosol forming substrate sheet
combining the rigid sheet with the aerosol forming substrate sheet for obtaining a second rigid susceptor sheet.

A method of manufacturing an inductively heatable consumable for aerosol generation, wherein before the step of cutting the rigid sheet in small size of particles, the method further comprising the step of:

perforating the aerosol forming substrate sheet and susceptor sheet.

The step of perforating the aerosol forming layer and the inductively heatable susceptor layer creates perforations which extend fully through the sheet, thus, through the resulting consumable. As noted above, the perforations facilitate air flow through the aerosol generating article during use in an aerosol generating device and may improve heating efficiency due to the skin effect. The perforations allow the porosity, and hence the air permeability, of the resultant aerosol generating article to be carefully controlled and optimised.

The step of perforating the layers of aerosol forming substrate and susceptor may be performed mechanically (for example by perforating rollers or by the abovementioned embossing rollers or debossing rollers), electrostatically or by laser.

DETAILED DESCRIPTION OF EMBODIMENTS

Embodiments of the present disclosure will now be described by way of example only and with reference to the accompanying drawings.

Figure 1:
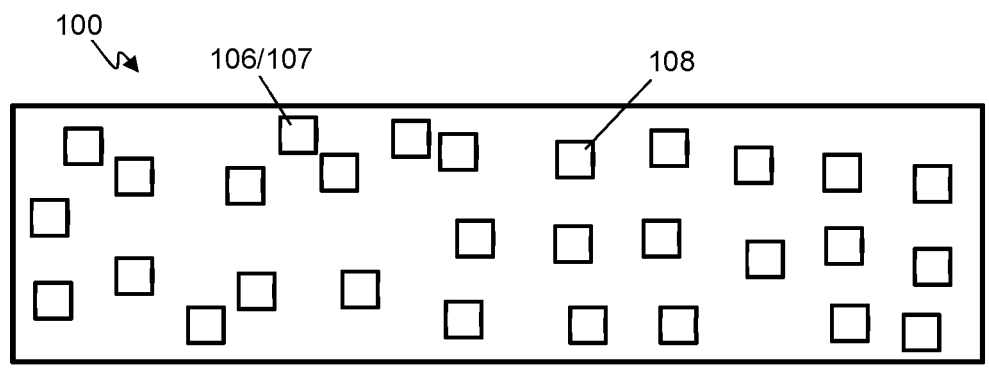
FIG. 1 is a schematic drawing of an inductively heatable tobacco consumable comprising particles of rigid susceptor and particles of aerosol forming substrate according to an aspect of the invention.

FIG. 1 gives a schematically view of an inductively heatable tobacco consumable 100 according to one aspect of the invention.

Figures 2, 3:
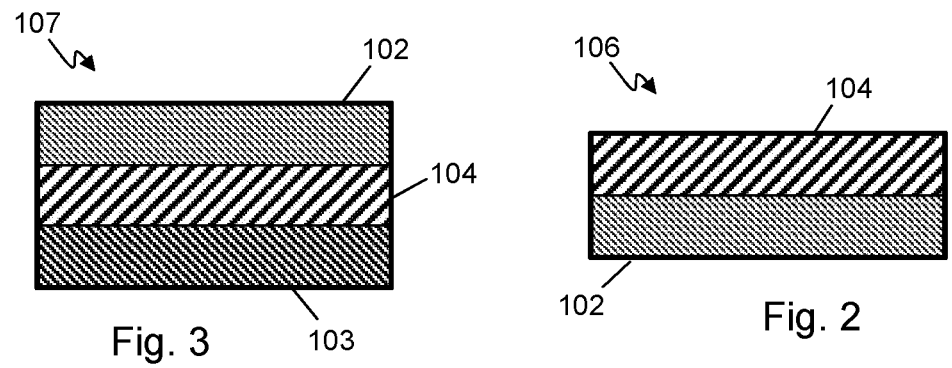
FIG. 2 is a side view of a rigid sheet of susceptor comprising a sheet of susceptor combined with a sheet of aerosol forming substrate according to one aspect of the invention.
FIG. 3 is a side view of a second rigid sheet of susceptor comprising a sheet of susceptor combined in the middle of two sheets of aerosol forming substrate.

FIG. 2 shows a sheet of rigid susceptor 106 comprising a sheet of susceptor 104 combined with a sheet of aerosol forming substrate 102.

Alternatively, in some embodiments, as shown in FIG. 3, a sheet of rigid susceptor 107 may comprise an additional sheet of aerosol forming substrate 103 combined with the rigid susceptor 106 such that the sheet of susceptor 104 stands in the middle of the first and second sheets of aerosol forming substrate 102 and 103, such that the sheet of susceptor 104 adheres to the first and second sheets of aerosol forming substrate 102 and 103. Alternatively, a sheet of rigid susceptor may be a combination of plurality of sheets 106, or a combination of plurality of sheets 107 or combination of plurality of sheets 106 and 107.

Adhering or combining includes technologies amongst printing, gluing, stacking, binding, sticking.

The inductively heatable susceptor layer 104 is thereby enclosed by the aerosol forming substrate layers. One advantage of this approach is that it may improve heating efficiency. Another advantage of this approach is that it may extend the shelf-life of the inductively heatable susceptor layer by virtue of the fact that the aerosol forming substrate layers 104 and 103 and adhesive may form a protective enclosure around the inductively heatable susceptor layer (e.g. comprising iron), thereby preventing oxidation of the inductively heatable susceptor (the thickness of the adhesive may be about 10 micrometres).

This maybe also the case for the embodiment of the present invention shown in FIG. 2.

The sheet of aerosol forming substrate 102 and/or 103 includes tobacco (which may have been processed in some way to form, for example, tobacco derivatives, expanded tobacco, tobacco extract, homogenized tobacco, tobacco substitutes or any combinations thereof, preferably reconstituted tobacco that is easy to manufacture).

The particles of aerosol forming substrate 108 include tobacco (which may also be processed to form, for example, tobacco derivatives, expanded tobacco, reconstituted tobacco, tobacco extract, homogenized tobacco, tobacco substitutes or any combinations thereof).

Turning back to FIG. 1, the consumable 100 comprises particles of aerosol forming substrate 108 and particles of rigid susceptor sheet 106 and/or 107.

The rigid susceptor particles 106 and/or 107 have a similar size and shape and as far as possible are distributed within the tobacco particles 108 in a consistent orientation relative to an induction coil. In the present embodiment, the susceptor particles are shaped as small discs. However, in alternative embodiments they could be shaped as annular discs. They could also be shaped as ribbons but in such a case it is more important to try to obtain a consistent orientation of the ribbons relative to the induction coil.

To produce the susceptor from which the susceptor particles 106 and 107 are formed, in some embodiments, a pre-formed aerosol forming substrate sheet is combined with pre-formed susceptor sheet. In various embodiments this is achieved by providing an adhesive between faces of the substrate sheet and the susceptor sheet that are to be abutted. Once abutted, due to the adhesive, or any other form of process by which the substrate sheet and the susceptor sheet are joined, the sheets are combined. Where there is a further aerosol forming substrate layer as in susceptor particles 107, a further aerosol forming substrate sheet is joined to an opposing side of the susceptor sheet to the side to which the other aerosol forming substrate is joined or to be joined. Regardless of the number of aerosol forming substrate sheets, this provides a sheet of rigid susceptor. This means no further processing needs to be carried out on the susceptor.

Due to the rigidity of the aerosol forming substrate sheet(s), and the corresponding rigidity of the susceptor sheet, the susceptor has sufficient shear strength to minimise curling when induction heating is applied. This is in part achieved by the various layers being pre-formed as sheets without needing to dry or cure any one layer when combining the layers or for one layer to be provided in a non-solid form that then requires further processing in order to cause the layer to set and provide the desired properties. With the susceptor being formed in the manner described, the desired properties are provided without a need for further processing. Further, should one layer be provided in a non-solid form during the process of combining the layers, that layer provided in the non-solid form would not have the desired rigidity, which could lead to variation in the rigidity thoughout the layer, and also between separate susceptors. This would cause a greater variation in the rigidity of susceptors without allowing the rigidity to be known before the susceptor is produced. By using pre-formed sheets, the rigidity of the sheets is able to be known before they are combined allowing each sheet to only be used if it meets a threshold rigidity, such as by having a minimum shear strength, and in some embodiments, a minimum uniformity of shear strength across the sheet.

Figure 5:
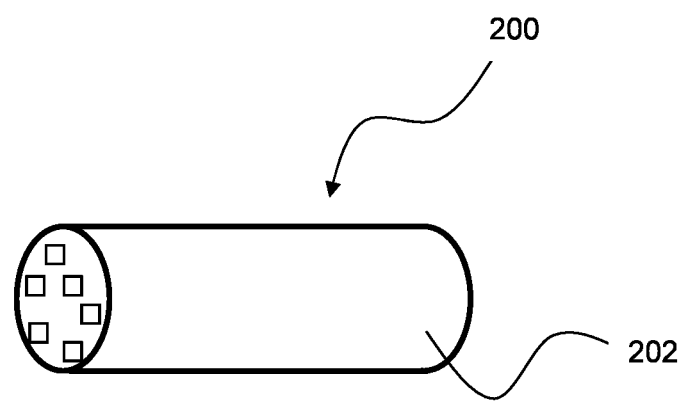
FIG. 5 is a side view of a rod including a mixture of rigid susceptor particles and particles of aerosol forming substrate wrapped by a paper sheet.

For forming the tobacco consumable 100 according to the invention, the sheet of rigid susceptor is cut into particles, providing sheared particles (where the layers have been sheared by the cutting process). In some embodiments, such particles are then mixed together with particles of aerosol forming substrate. The resultant mixture may be wrapped by a wrapper such as a paper sheet 202 to form a rod 200, shown in FIG. 5. Such a continuous rod 200 is then cut to the required size for a tobacco plug to be used in combination with an inductive heating device 400 for aerosol generation.

Figure 6:
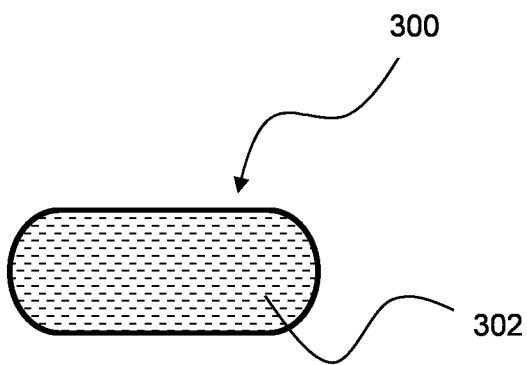
FIG. 6 is a side view of a capsule including a mixture of rigid susceptor particles and particles of aerosol forming substrate.

Alternatively, the resultant mixture may be put in a capsule 300 (shown in FIG. 6) to be used in combination with an inductive heating device 400 for aerosol generation. The capsule may have at least one porous side 302 to allow airflow.

Figure 4:
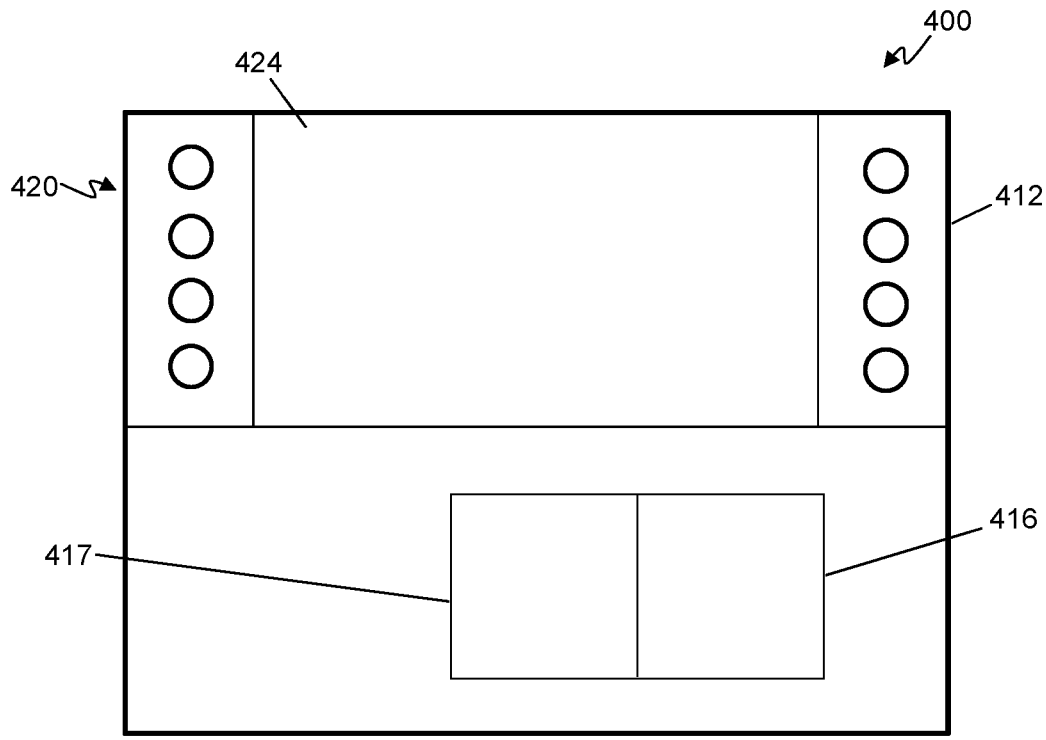
FIG. 4 is a diagrammatic illustration of part of an aerosol generating device according to the present disclosure.

Referring to FIG. 4, there is shown diagrammatically a vapour generating device 400 according to an example of the present disclosure. The vapour generating device 400 comprises a housing 412. The device 400 includes a power source 416 and control circuitry 417, which may be configured to operate at high frequency. The power source typically comprises one or more batteries which could, for example, be inductively rechargeable. The device 400 also includes an air inlet (not shown).

The vapour generating device 400 comprises an induction heating assembly 420 for heating a vapour generating (i.e. vaporisable) substance. The induction heating assembly 420 comprises a generally cylindrical heating compartment 424, which is arranged to receive a correspondingly shaped generally cylindrical induction heatable capsule 300 or rod 200 as described above. The induction heatable capsule 300 typically comprises an outer layer or membrane, with the outer layer or membrane being air permeable. For example, the induction heatable capsule 300 may be a disposable capsule containing the mixture of particles of aerosol forming substrate and particles of induction heatable rigid susceptor.

REFERENCE NUMBERS USED FOR THE FIGURES

100 Consumable
102 First aerosol forming substrate sheet
103 Second aerosol forming substrate sheet
104 Susceptor sheet
106 First rigid susceptor sheet
107 Second rigid susceptor sheet
108 Particles of aerosol forming substrate
400 Aerosol vapour device
412 Housing
416 Power source
417 Control circuitry
420 Induction heating assembly
424 Heating compartment
430 Induction coil

The invention claimed is:

1. An inductively heatable consumable for aerosol generation, the consumable comprising flavour forming particles and a susceptor in the form of susceptor particles, wherein each susceptor particle is a combination of a rigid aerosol forming substrate layer and a susceptor layer that together make the susceptor particle rigid, wherein the rigid aerosol forming substrate layer has a rigidity greater than a rigidity of the susceptor layer.

2. The inductively heatable consumable for aerosol generation according to claim 1, wherein each rigid susceptor particle has a rigidity not more than 10% more rigid than the rigidity of the rigid aerosol forming substrate layer.

3. The inductively heatable consumable for aerosol generation according to claim 2, wherein the rigidity of each rigid susceptor particle is not more than 5% more rigid than the rigidity of the rigid aerosol forming substrate layer.

4. The inductively heatable consumable for aerosol generation according to claim 3, wherein the rigidity of each rigid susceptor particle is not more than 1% more rigid than the rigidity of the rigid aerosol forming substrate layer.

5. The inductively heatable consumable for aerosol generation according to claim 1, wherein the susceptor has a shear strength of at least 250 MPa.

6. The inductively heatable consumable for aerosol generation according to claim 1, wherein each susceptor particle includes perforations extending through the layers.

7. The inductively heatable consumable for aerosol generation according to claim 1, wherein the combination of each susceptor particle further includes a second aerosol forming substrate layer.

8. The inductively heatable consumable for aerosol generation according to claim 7, wherein the rigidity of each rigid susceptor particle with the second aerosol forming substrate is substantially equivalent to or greater than the rigidity of each rigid susceptor particle without the second aerosol forming substrate.

9. The inductively heatable consumable for aerosol generation according to claim 7, wherein each susceptor particle includes perforations extending through all of the layers.

10. The inductively heatable consumable for aerosol generation according to claim 1, wherein each susceptor particle is printed, or wherein each susceptor particle includes a glue layer between the rigid aerosol forming substrate layer and the susceptor layer.

11. The inductively heatable consumable for aerosol generation according to claim 1, wherein susceptor particle and the flavour forming particles are homogeneously mixed.

12. The inductively heatable consumable for aerosol generation according to claim 1, wherein the rigid susceptor particles are shaped as discs.

13. The inductively heatable consumable for aerosol generation according to claim 1, wherein shapes of the rigid particles and of the flavour forming particles includes line, strand, polygonal, square, curve, disc, oval, annulus, circle.

14. The inductively heatable consumable for aerosol generation according to claim 1, wherein the flavour forming particles and the rigid aerosol forming substrate layer include tobacco, tobacco derivatives, expanded tobacco, tobacco extract, homogenized tobacco, tobacco substitutes, reconstituted tobacco including tobacco and any one or more of cellulose fibres, tobacco stalk fibres and inorganic fillers such as calcium carbonate, or any combinations thereof.

15. The inductively heatable consumable for aerosol generation according to claim 7, wherein the flavour forming particles, the rigid aerosol forming substrate layer, and the second aerosol forming substrate layer each include tobacco, tobacco derivatives, expanded tobacco, tobacco extract, homogenized tobacco, tobacco substitutes, reconstituted tobacco including tobacco and any one or more of cellulose fibres, tobacco stalk fibres and inorganic fillers such as calcium carbonate, or any combinations thereof.

16. The inductively heatable consumable for aerosol generation according to claim 1, wherein the susceptor particles and the flavour forming particles range in length and/or diameter from 1 to 15 millimetres.

17. The inductively heatable consumable for aerosol generation according to claim 16, wherein the susceptor particles and the flavour forming particles range in length and/or diameter from 2 to 8 millimetres.

18. The inductively heatable consumable for aerosol generation according to claim 1, further comprising a paper sheet wrapped around the flavour forming particles and the susceptor particles to form a rod.

19. The inductively heatable consumable for aerosol generation according to claim 1, further comprising a capsule in which the flavour forming particles and the susceptor particles are received.

20. The inductively heatable consumable for aerosol generation according to claim 19, wherein the capsule is porous in at least one side.

21. An aerosol generating device comprising:
- the consumable according to claim 1;
- a heating compartment arranged to receive the consumable;
- an induction heating assembly arranged to inductively heat the consumable.

22. A method of manufacturing an inductively heatable consumable for aerosol generation, the method comprising steps of:
- providing an aerosol forming substrate sheet;
- providing a susceptor sheet;
- combining the susceptor sheet with the aerosol forming substrate sheet for obtaining a rigid sheet;
- cutting the rigid sheet into particles;
- mixing said particles with particles of an aerosol forming substrate.

23. The method of manufacturing an inductively heatable consumable for aerosol generation according to claim 22, wherein before the step of cutting the rigid sheet into particles, the method further comprises the steps of:
- providing a second aerosol forming substrate sheet; and
- combining the second aerosol forming substrate sheet with the susceptor sheet and the aerosol forming substrate sheet to form the rigid sheet.

24. The method of manufacturing an inductively heatable consumable for aerosol generation according to claim 22, wherein before the step of cutting the rigid sheet into particles, the method further comprising the step of:
- perforating the aerosol forming substrate sheet and the susceptor sheet.

25. The method of manufacturing an inductively heatable consumable for aerosol generation according to claim 22, wherein the step of combining includes printing, gluing, stacking, binding, and/or sticking the susceptor sheet with the aerosol forming substrate sheet.

26. The inductively heatable consumable for aerosol generation according to claim 1, wherein the rigid aerosol forming substrate layer is a portion of a sheet, and the susceptor layer is a portion of a sheet.

27. An inductively heatable consumable for aerosol generation, the consumable comprising particles of an aerosol forming substrate mixed with a susceptor in the form of susceptor particles, wherein each susceptor particle is a combination of a rigid aerosol forming substrate layer and a susceptor layer that together make the susceptor particle rigid, wherein the rigid aerosol forming substrate layer has a rigidity greater than a rigidity of the susceptor layer.

* * * * *

UNITED STATES PATENT AND TRADEMARK OFFICE
CERTIFICATE OF CORRECTION

PATENT NO. : 11,700,874 B2
APPLICATION NO. : 16/957644
DATED : July 18, 2023
INVENTOR(S) : Robert Alizon, Peter Uhrmeister and Andrew Robert John Rogan Page 1 of 1

It is certified that error appears in the above-identified patent and that said Letters Patent is hereby corrected as shown below:

On the Title Page

Column 1, insert:
-- (30) EP 17211198 Filed December 29, 2017. --

Signed and Sealed this
Tenth Day of September, 2024

Katherine Kelly Vidal
*Director of the United States Patent and Trademark Office*